US00PP12942P2

(12) United States Plant Patent
Zaiger et al.

(10) Patent No.: US PP12,942 P2
(45) Date of Patent: Sep. 10, 2002

(54) CHERRY TREE NAMED 'MINNIE ROYAL'

(76) Inventors: Chris Floyd Zaiger, 1207 Grimes Ave.; Gary Neil Zaiger, 4005 California Ave.; Leith Marie Gardner, 1207 Grimes Ave.; Grant Gene Zaiger, 4005 California Ave., all of Modesto, CA (US) 95358

( * ) Notice: Subject to any disclaimer, the term of this patent is extended or adjusted under 35 U.S.C. 154(b) by 0 days.

(21) Appl. No.: 09/535,462

(22) Filed: Mar. 27, 2000

(51) Int. Cl.[7] ..... A01H 5/00
(52) U.S. Cl. ..... Plt./181
(58) Field of Search ..... Plt./181

*Primary Examiner*—Bruce R. Campell
*Assistant Examiner*—Anne Marie Grünberg

(57) ABSTRACT

A new and distinct variety of cherry tree (*Prunus avium*) that has the following unique combination of features that are desirable in a new variety. The following features of the tree and its fruit are characterized with the tree budded on 'Mahaleb' Rootstock (non-patented), grown on Hanford sandy loam soil with Storie Index rating 95, in USDA Hardiness Zone 9, near Modesto, Calif., and with standard commercial cultural fruit growing practices, such as, pruning, thinning, spraying, irrigation and fertilization.

1. Vigorous, upright growth.

2. Early maturity of firm fruit.

3. Heavy and regular production of medium size fruit.

4. Fruit with an attractive red skin color.

5. Fruit with good flavor and eating quality.

6. Early blooming with a low winter chilling requirement of approximately 500 hours at or below 45° F.

7. The ability of the fruit to remain firm on the tree 10 days past maturity (shipping ripe).

1 Drawing Sheet

FEDERALLY SPONSORED RESEARCH OR DEVELOPMENT

Not applicable.

BACKGROUND AND FIELD OF THE INVENTION

In the field of plant genetics we conduct an extensive and continuing plant-breeding program including the origination and sexual reproduction of orchard trees, and of which interspecifics, plums, peaches, nectarines, apricots and cherries are exemplary. It is against this background of our activities that the present variety of cherry tree was originated and asexually reproduced by budding to 'Mahaleb' Rootstock (non-patented), as performed by us in our experimental orchard near Modesto, Stanislaus County, Calif.

ORIGIN OF THE VARIETY

The present new variety of cherry tree (*Prunus avium*) was originated by us in our experimental orchard located near Modesto, Calif., as an open pollinated seedling from a seedling selection with the field identification number 6HB480 (non-patented). 6HB480 originated as an open pollinated seedling selection of 17H143 (non-patented). 17H143 is a first generation cross between 26W232 (non-patented) and a low chilling cherry seedling of unknown parentage. The maternal parent (26W232) is a selected seedling from an open pollinated 'Bing' Cherry tree (non-patented). A large group of these open pollinated seedlings were grown on their own root system, and maintained under close observation, one such low chilling, early maturing seedling, which is of the present variety, having especially desirable fruit characteristics, was selected for asexual reproduction and commercialization.

ASEXUAL REPRODUCTION OF THE VARIETY

Asexual reproduction of the new variety of cherry tree (*Prunus avium*) was by budding to 'Mahaleb' Rootstock (non-patented), a standard rootstock for cherries in California, as performed by us in our experimental orchard located near Modesto, Calif., and shows that reproductions run true to the original tree and all characteristics of the tree and its fruit are established and transmitted through succeeding asexual propagations.

SUMMARY OF THE VARIETY

The new and distinct cherry tree is of large size, vigorous, upright growth, and has a low winter chilling requirement of approximately 500 hours below 45° F. The tree is a regular and productive bearer of early maturing, medium size fruit with good flavor and eating quality. The fruit is further characterized by its attractive red skin color, its firmness, its good handling and shipping qualities, and the ability to remain firm on the tree 10 days past maturity (shipping ripe). In comparison to the 'Early Burlat' Cherry tree (non-patented), the new variety has a lower winter chilling requirement and is 10 days earlier in blooming giving it a wider range of adaptibility to grow in warmer areas with less winter chilling. The fruit has firmer flesh, greater handling and shipping quality, and is approximately 2 days later in maturity.

PHOTOGRAPH DESCRIPTION OF THE VARIETY

The accompanying color photographic illustration shows typical specimens of the foliage and fruit of the present new cherry variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of cherry tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:

*Size.*—Large. Tree height at maturity pruned 12 to 15 feet in height for economical fruit harvesting.

*Vigor.*—Moderately vigorous. Tree growth reaching 4 to 6 feet in height the first growing season. Growth rate will vary slightly with type and depth of soil, cultural practices and climatic conditions.

*Form.*—Upright. During the first and second growing season branches are selected, which become the scaffolds, and are tied downward to increase crotch angle and help spread the tree to the desired width of 12 to 14 feet.

*Productivity.*—Very productive. Produces adequate fruit set annually.

*Bearer.*—Regular, adequate fruit set for 11 years. Amount of fruit set varies with the number of pollinator trees per acre, climatic conditions and cultural practices.

*Density.*—Medium dense. The number of branches and leaves that grow through the center of the tree restrict the amount of sunlight and air movement. Pruning to open the center of the tree (vase shape) is desirable to provide more sunlight and air movement to enhance fruit color and keep fruit spurs healthy.

*Hardiness.*—Tree grown in USDA Hardiness Zone 9. Winter chilling requirement is approximately 500 hours at or below 45° F.

Trunk:

*Size.*—Large. Measured 18 inches in circumference at 16 inches above ground on an 8 year old tree.

*Texture.*—Medium stocky.

*Color.*—Grayish brown to brown (5-E-2) to (5-F-5).

Branches:

*Size.*—Medium. Average circumference 9 inches measured 36 inches above ground.

*Texture.*—Smooth to medium rough, varies with age of growth.

*Lenticels.*—Large size. Medium number, average 18 lenticels within a 4 square inch area, measured 36 inches above ground. Varies from 1/8 to 3/8 inch in length. Varies from 1/32 to 3/32 inch in width.

*Color.*—Light brown to brown (5-D-4) to (5-E-4). Varies with age of growth.

Leaves:

*Size.*—Large. Average length 7 inches. Average width 2 1/8 inches.

*Form.*—Varies between ovate and lanceolate, pointed.

*Margin.*—Double serrate, giving a very distinctive leaf margin.

*Thickness.*—Medium.

*Surface.*—Smooth.

*Petiole.*—Average length 1 5/8 inches. Average width 3/32 inch. Color—upper surface—strawberry red to violet brown (10-D-8) to (10-F-8). Lower surface — bile yellow to leaf green (30-C-5) to (30-D-6).

*Glands.*—Reniform. Size—large. Number varies from 2 to 6 . Average number 2. Located on base of leaf blade and upper portion of petiole. Color varies from brownish red to garnet brown (9-D-6) to (9-D-8).

*Color.*—Upper surface—green to deep green (28-E-4) to (28-E-7). Lower surface—grayish green to green (29-D-5) to (29-D-7).

Flower buds:

*Number per spur.*—Average 4, varies from 1 to 6.

*Size.*—Large. Average length 7/16 inch. Average width 15/64 inch.

*Form.*—Plump, conical.

*Color.*—Varies from white (10-A-1) to very light pinkish white (10-A-2) on upper surface of petal.

*Peduncle.*—Average length 3/4 inch. Average width 1/16 inch.

*Hardiness.*—Hardy in all stone fruit growing areas of California.

Flowers:

*Number per flower bud.*—Average 4, varies from 1 to 6.

*Size.*—Large. Average height 4/5 inch. Average diameter 1 2/5 inches.

*Petal.*—Nearly orbicular, narrows at point of attachment. Outer edge slightly cleft. Average length 3/5 inch. Average width 31/64 inch.

*Pistil* —Number per flower—usually one. Average length 45/64 inch. Color—yellowish white to pale yellow (3-A-2) to (3-A-3).

*Stamens.*—Number per flower 30 to 36. Average filament length 19/32 inch. Filament color—white (1-A-1). Anther color—light yellow to maize yellow (4-A-4) to (4-A-6).

*Pollen* —Present, pollinator required—not self-fruitful. Color—light yellow to maize yellow (4-A-4) to (4-A-6).

*Pedicel.*—Long length. Average length 1 1/8 inches. Average width 1/16 inch.

*Aroma.*—None.

*Blooming period.*—Date of First Bloom Mar. 2, 1997. Date of Full Bloom Mar. 10, 1997. Varies slightly with climatic conditions.

*Color.*—White (1-A-1). Before the flowers open, the top edge of the petals are tinged with rose-pink (12-A-5) to (12-A-6), after the flowers open, the pink fades to white.

Fruit:

*Maturity when described.*—Firm ripe.

*Date of first picking.*—May 1, 1997.

*Date of last picking.*—May 8, 1997. Varies slightly with climatic conditions.

*Size.*—Medium. Comparatively uniform. Average diameter axially 1 inch. Average transversely in suture 7/8 inch. Average weight 9.4 grams. Average weight and size varies slightly with fertility of the soil, amount of fruit set and climatic conditions.

*Form.*—Oblate.

*Suture.*—Shallow, relatively smooth.

*Ventral surface.*—Nearly rounded.

*Apex.*—Rounded to slight depression.

*Base.*—Retuse.

*Cavity.*—Circular. Average depth 1/16 inch. Average breadth 3/16 inch.

Stem of fruit:

*Size.*—Medium thickness. Average length 1¾ inches. Average width 1/16 inch.

*Color.*—Green to leaf green (30-D-4) to (30-D-6).

Flesh:

*Ripens.*—Evenly.

*Texture.*—Firm, crisp.

*Fibers.*—Few, small and tender.

*Aroma.*—Moderate.

*Amygdalin.*—Undetected.

*Juice.*—Moderate.

*Eating quality.*—Good.

*Flavor.*—Good.

*Color.*—Rose pink to red (11-A-4) to (11-A-6), varies with fruit maturity. Pit cavity — deep red to wine red (11-C-8) to (11-D-8).

*Brix.*—18.2° average.

Skin:

*Thickness.*—Medium.

*Texture.*—Medium, tenacious to flesh.

*Down.*—Wanting.

*Tendency to crack.*—None during dry weather. Slight tendency to crack during wet weather, varies with stage of fruit maturity.

*Color.*—Red to wine red (11-D-6) to (11-D-8).

Stone:

*Type.*—Clingstone.

*Size.*—Average length 7/16 inch. Average width 5/16 inch. Average thickness ¼ inch.

*Form.*—Oblong.

*Base.*—Round.

*Apex.*—Round to slight apical point.

*Sides.*—Varies from equal to unequal. Some stones having one side extending a greater distance from the suture plane.

*Tendency to split.*—None.

*Ridges.*—Two small narrow ridges running along each side of the suture.

*Color.*—Light tan to tan (5-C-4) to (5-C-5).

Use: Dessert. Market, local and long distance.

Keeping quality: Good. Holds well in cold storage for 10 days and maintains good firmness and eating quality.

Shipping quality: Good. Minimal bruising or scarring in packing and shipping trials.

Plant disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of cherry tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of cherry tree, substantially as illustrated and described, characterized by its large size, vigorous, upright growth, having a low winter chilling requirement of approximately 500 hours at or below 45°, and being a regular and productive bearer of medium size, early maturing fruit; the fruit is also characterized by its firm, crisp flesh with an attractive red skin color, having good handling and shipping qualities, the ability to remain firm on the tree 10 days past maturity, good flavor and eating quality and, in comparison to 'Early Burlat' Cherry (non-patented), the new variety blooms approximately 10 days earlier and the fruit is approximately 2 days later in maturity.

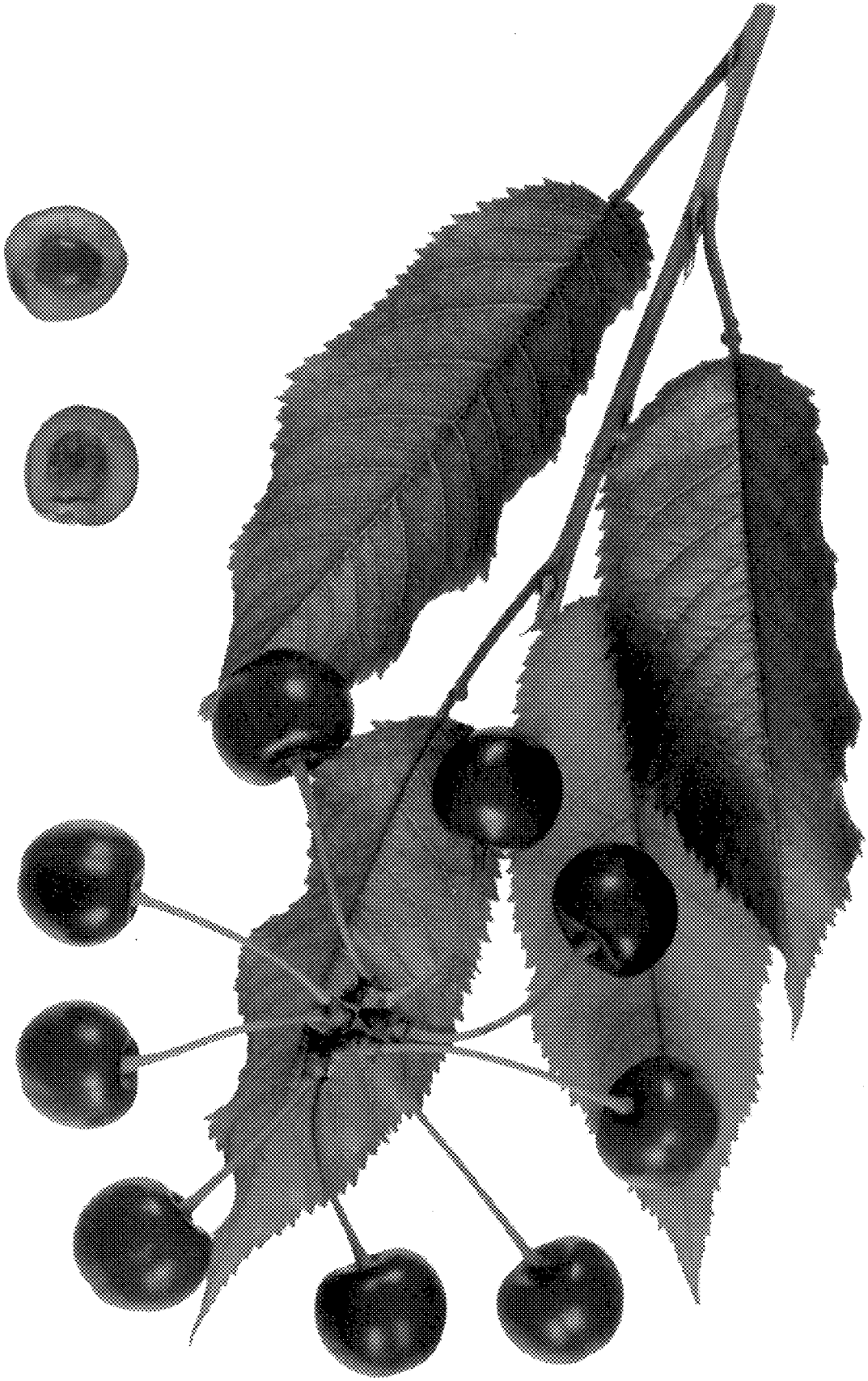

* * * * *